United States Patent [19]
Rosser, Jr. et al.

[11] Patent Number: 5,792,897
[45] Date of Patent: Aug. 11, 1998

[54] HYDROCARBON RECOVERY FROM CORROSIVE EFFLUENT STREAM

[75] Inventors: Frank Samuel Rosser, Jr., La Grange Park; Jill Marie Meister, Elk Grove Village, both of Ill.

[73] Assignee: UOP LLC, Des Plaines, Ill.

[21] Appl. No.: 756,569

[22] Filed: Nov. 26, 1996

Related U.S. Application Data

[63] Continuation of Ser. No. 311,238, Sep. 23, 1994, abandoned.

[51] Int. Cl.$^6$ .................. C07C 7/12; C10G 67/06
[52] U.S. Cl. .................. 585/738; 585/743; 585/747; 585/823; 585/826; 585/820; 208/99; 208/140; 208/299; 208/305
[58] Field of Search .................. 208/99, 100, 103, 208/105, 139, 140, 299, 305; 585/738, 743, 747, 820, 823, 826

[56] References Cited

U.S. PATENT DOCUMENTS

| | | | |
|---|---|---|---|
| 2,943,041 | 6/1960 | Johnston et al. | 208/105 |
| 3,238,123 | 3/1966 | Voorhies, Jr. et al. | 585/823 |
| 3,365,394 | 1/1968 | Cottle | 585/826 |
| 3,506,409 | 4/1970 | Hutson, Jr. et al. | 585/823 |
| 3,862,900 | 1/1975 | Reusser | 585/823 |
| 3,864,243 | 2/1975 | Reusser et al. | 585/823 |
| 3,917,733 | 11/1975 | Winter, III | 585/823 |
| 4,786,625 | 11/1988 | Imai et al. | 502/326 |
| 4,831,206 | 5/1989 | Zarchy | 585/737 |
| 5,082,987 | 1/1992 | Olbrich et al. | 585/826 |
| 5,146,037 | 9/1992 | Zarchy et al. | 585/738 |
| 5,164,076 | 11/1992 | Zarchy et al. | 585/823 |
| 5,238,555 | 8/1993 | Pappas et al. | 208/340 |
| 5,245,102 | 9/1993 | Zarchy et al. | 585/738 |
| 5,271,835 | 12/1993 | Gorawara et al. | 208/305 |
| 5,292,987 | 3/1994 | Zarchy et al. | 585/738 |
| 5,336,834 | 8/1994 | Zarchy et al. | 585/737 |

OTHER PUBLICATIONS

Perr's Chemical Engineers' Handbook. pp. 12–28, 1984.

*Primary Examiner*—Walter D. Griffin
*Attorney, Agent, or Firm*—Thomas K. McBride; John G. Tolomei

[57] ABSTRACT

An adsorption arrangement in combination with a catalytic hydrocarbon conversion process suspends non-hydrocarbon materials that act to enhance the operation of the conversion zone by using an adsorption zone arrangement to keep the compounds in recirculation about the reaction zone and integrates the adsorption zone arrangement with a chiller to increase the recovery of $C_4$ hydrocarbons. The process of this invention is particularly useful for the isomerization of hydrocarbons wherein the adsorption zone arrangement operates to maintain chloride compounds in the reaction zone and to prevent contamination of product streams with the chloride compounds while increasing the recovery of $C_4$ hydrocarbons. This invention can be used in combination with traditional adsorptive methods of removing contaminant from feedstreams that enter reaction zones.

14 Claims, 2 Drawing Sheets

HYDROCARBON RECOVERY FROM CORROSIVE EFFLUENT STREAM

CROSS REFERENCE TO RELATED APPLICATION

This application is a continuation of U.S. Ser. No. 08/311,238, filed Sep. 23, 1994 now abandoned.

BACKGROUND OF THE INVENTION

FIELD OF THE INVENTION

This invention relates generally to the catalytic conversion of hydrocarbon containing feedstreams and the separation and recovery of hydrocarbons from the conversion zone effluent. More specifically this invention relates to the separation of conversion zone effluents that contain mobile additives.

DESCRIPTION OF THE PRIOR ART

Numerous hydrocarbon conversion processes are widely used to alter the structure or properties of hydrocarbon streams. For example, hydrotreating is a common method for the upgrading of feedstocks by the removal of contaminants such as sulfur. Isomerization processes rearrange the molecular structure from straight chain paraffinic or olefinic hydrocarbons to more highly branched hydrocarbons that generally have a higher octane rating or increased utility as substrates for other conversion processes. Hydrocarbon dehydrogenation processes are well known conversion processes. Hydrocarbon dehydrogenation processes are well known methods of producing olefinic or aromatic substrates. Additional processes include alkylation, transalkylation, reforming and others. Operating conditions and methods for carrying out these processes are well known by those skilled in the art. Well known methods for operating such processes include the adsorptive removal of contaminants from feedstreams and the desorption of contaminants into resulting effluents or product fractions. U.S. Pat. No. 4,831,206 describes one such arrangement for the adsorption of sulfur compounds and is hereby incorporated by reference.

Many of these processes share the common feature of using a catalyst in the presence of one or more materials that enhance the effectiveness of the catalyst in the reaction zone. These performance enhancing materials can operate in many ways such as increasing or attenuating catalyst activity, neutralizing catalyst poisons, or solubilizing catalyst or feed contaminants. Such performance enhancement materials may be chemically or physically sorbed on the catalyst or dispersed in the hydrocarbon stream.

Where the hydrocarbon product stream leaving a hydrocarbon conversion zone contains the performance enhancing material or beneficent material, methods are known for preventing contamination of the hydrocarbon product with the beneficent material and the loss of this beneficent material to the product stream. For example, light paraffin dehydrogenation catalysts containing platinum, tin and germanium components have their activity attenuated with sulfur compounds. A description of such catalysts can be found in U.S. Pat. No. 4,786,625, the contents of which are hereby incorporated by reference. The effluent from the dehydrogenation zone can carry the sulfur compounds into downstream processes and products. Those skilled in the art will recognize a variety of other processes where the materials useful in a catalytic conversion zone degrade products or process operations by their exit from the conversion zone into the effluent streams.

2

Isomerization of hydrocarbons presents another case where contamination of a catalyst promoter material poses concern. Many isomerization processes employ a highly effective chlorided platinum alumina catalyst system in the reaction zone. The chlorided catalyst requires a continual addition of chloride to replace chloride lost from the surface of the catalyst into the product stream. Hydrogen chloride and/or volatile organic chlorides escape from the process with a stabilizer overhead stream and, apart from the loss of chloride, pose environmental concern. In addition to the loss of chlorides and environmental concerns, chloride loss hinders the operation of chloride promoted isomerization zones in other ways. For example, the recycle of hydrogen or hydrocarbons by a zeolitic adsorption process is not practical when a chloride type catalyst is used unless hydrogen chloride is removed from the recycle stream. Hydrogen chloride produced by the addition of chloride to the reaction zone or released from the catalyst composite results in significant amounts of hydrogen chloride leaving the effluent from the isomerization zone. Contact of this hydrogen chloride with the crystalline alumino-silicates in adsorption or conversion zones will decompose the matrix structure of many crystalline alumino-silicates thereby destroying any catalytic or adsorptive function. Therefore, absent chloride neutralization methods, chlorided catalyst systems generally have insufficient compatibility with many zeolitic catalysts or adsorbents to permit simultaneous use.

U.S. Pat. No. 5,336,834 issued to Zarchy et. al., the contents of which are hereby incorporated by reference, discloses a method of recovering chlorides or other compounds that are beneficially present in a reaction zone from the reaction zone effluent for return and reuse in the reaction zone.

Apart from the recovering of additives or other beneficial compounds from conversion zone effluents, such effluents routinely undergo separation steps to recover products and recycle streams. Well known processing procedures for hydrogen containing effluent streams include steps to remove potentially valuable C3+ hydrocarbons from the hydrogen containing gas streams. U.S. Pat. No. 5,238,555, the contents of which are hereby incorporated by reference, and the references discussed therein disclose a number of arrangements for purifying a hydrogen stream and recovering C3+ product hydrocarbons from a conversion zone effluent stream. These arrangements rely on refrigeration to chill a gaseous portion of the conversion zone effluent stream. Chilling of the gaseous portion of the effluent stream alters the thermodynamic equilibrium of the gas thereby causing the heavier and more valuable hydrocarbons to condense.

A broad object of this invention is to integrate the steps for recovery of additives with separation steps for recovering liquefiable hydrocarbons from gas streams.

A further object of this invention is to improve methods for the reaction of hydrocarbon feedstreams with chloride promoted catalyst systems by retaining chloride promoter, minimizing chloride contamination and increasing the recovery of valuable hydrocarbon products.

SUMMARY OF THE INVENTION

It has now been discovered that an adsorption arrangement can be integrated into a hydrocarbon recovery arrangement to act in combination with a catalytic hydrocarbon conversion arrangement for retaining non-hydrocarbon materials that are returned to the conversion zone to enhance its operation. Thus, this invention enhances the conversion zone operation by keeping beneficial additive compounds in circulation while increasing the efficiency of the hydrocarbon recovery section. This arrangement uses a portion of a feed component stream to the hydrocarbon conversion zone as a coolant stream. The coolant stream at least partially cools a refrigerant that chills a portion of the reaction zone effluent. This advantageous arrangement for chilling permits recovery of additional hydrocarbon components. The cooling of the refrigerant provides heat to the feed component stream so that it also serves as a regenerant stream for recovering adsorbed additive compounds and returning the additive compounds to the conversion zone.

This invention has application to numerous hydrocarbon conversion processes. A basic requirement for using the process is a hydrocarbon conversion zone that produces a $C_3$ and $C_4$ hydrocarbon containing effluent stream and operates in the presence of non-hydrocarbon material which is carried out of the conversion zone by the effluent stream. Examples of mobile additive materials that can escape with an effluent stream and enhance the operation of a reaction zone include $H_2S$ and $HCl$. This invention is particularly useful for isomerization processes and in particular a $C_4$ isomerization process.

In order to effect this process, an adsorbent material must have adsorption capacity for the additive material in the presence of the hydrocarbon effluent and one of the input streams to the conversion zone must be capable of desorbing the additive material from the adsorbent. The invention is not limited to any particular type of adsorbent; any material with the necessary capacity may be used. Preferably, the adsorbent material will recover 90 wt. % and, more preferably, more than 99 wt. % of the additive material in the effluent or effluent fraction. The typical adsorbents for use in the invention include molecular sieves, silicalite, silica gels, activated carbon, activated alumina and the like. Reference is made to zeolitic molecular sieves by Donald W. Breck (John Wiley & Sons, 1974) which describes the use and selection of zeolite adsorbents and which is incorporated herein by reference. Of course the adsorption and desorption capacity for the beneficial material must exist under a reasonable range of conditions. Preferably, the process conditions of the input and output stream will compliment the adsorption and desorption requirements of the adsorbent.

In general, operating conditions in many hydrocarbon conversion processes will enhance the operation of this invention. The compatibility of the typical operating conditions of many reaction zone inlet and outlet stream temperatures with the desorption and adsorption stages of this invention advantageously reduces operating costs. A majority of hydrocarbon conversion processes will operate with a relatively hot feedstream and a relatively cooler effluent stream or effluent stream fraction. The temperature differences between the reaction zone inlet stream and the outlet stream or outlet stream fraction provide a high temperature stream for desorption upstream of the reaction zone and a relatively lower temperature stream for downstream adsorption. By using a suitable adsorbent, the instant invention not only provides a means to sustain the level of beneficial material in the reaction zone, but also achieves it with very little utility cost. Endothermic processes provide especially suitable process conditions for the adsorption and desorption cycle wherein the high inlet temperatures facilitate desorption and the low outlet temperatures aid in adsorption. Where the feedstream and/or effluent stream receive one or more stages of heating and cooling, it is possible to select streams having suitable adsorption and desorption temperatures and thereby provide the beneficent material suspension of this invention with a minimum of utility costs.

The hydrocarbon recovery portion of this process, which is integrated with additive recovery and hydrocarbon conversion portions of this process, operates to separate and recover $C_4$ hydrocarbons from the lighter hydrocarbons in the effluent stream. In a typical recovery arrangement a stabilizer removes a majority of the $C_4$ hydrocarbons while small and difficult to recover amounts of $C_4$ hydrocarbons exit the stabilizer with an off-gas stream. The manner of chilling the offgas stream to alter its thermodynamic equilibrium is uniquely integrated into the process by using a stream containing reactants to cool the compressed refrigerant. Cooling of the refrigerant supplies heat to the reactant stream for desorption of the additive compound from the adsorption zone. Thus, by this invention the reactant stream supplies three functions of cooling a refrigerant, desorbing an additive and carrying the additive into the conversion zone.

The hydrocarbon recovery zone of this invention may be enhanced by incorporating other separation methods with the chilling of the off-gas. More complete recovery may be effected by the use of a suitable sponge oil to enhance the separation and recovery of $C_4$ hydrocarbons from the conversion process off-gases. In addition, the separation and recovery steps may include additional steps further chilling the recovered light gas components to recover higher purity hydrogen streams.

This invention is not limited to the recovery and recirculation of a single additive component about a reaction zone, but may include arrangements for the recovery and circulation of two or more components. Preferably a single adsorbent material in a single adsorption zone will retain all of the materials to be adsorbed from an effluent stream and desorbed into an inlet stream. Where necessary, multiple adsorbents in a single adsorption zone or multiple adsorption zones (with a single adsorbent material in each zone) may be used to recover the material from the reaction zone effluent stream. In cases of multiple adsorbents, the relative selectivity of the adsorbents pose problems of readsorption of one component from the inlet stream that has desorbed the component from an upstream adsorbent. In such cases the feed may be split to separately desorb components from each adsorbent and then recombined downstream of the desorption steps.

Accordingly, in one embodiment this invention is a process for recovering $C_4$ and heavier hydrocarbons from the effluent of a catalytic hydrocarbon conversion process. The process employs a mobile additive in a reaction zone and produces an effluent comprising $C_4$ hydrocarbons and $C_3$ and lighter hydrocarbons. The process contacts a first stream comprising hydrocarbons with a catalyst in the reaction zone in the presence of the additive material at hydrocarbon conversion conditions to convert hydrocarbons and produce a second stream comprising $C_4$ hydrocarbons, $C_3$ hydrocarbons, and the additive material. Separation of the second stream produces a liquid phase and a gaseous phase that comprises $C_4$ hydrocarbons, $C_3$ hydrocarbons, and the additive material. A gaseous input stream comprising at least a portion of the gaseous stream passes to an adsorption zone containing an adsorbent having an adsorption capacity for the additive material wherein the adsorbent contacts the gaseous input stream at adsorption conditions to adsorb the additive material on the adsorbent and produce a gaseous effluent stream having a reduced concentration of the additive material relative to the gaseous input stream and an adsorbent loaded with the additive material. Indirect heat exchange with at least a portion of a refrigerant stream chills at least a portion of the gaseous effluent stream to produce a chilled stream. Separation of the chilled stream produces a light gas stream comprising $C_3$ hydrocarbons and lower boiling compounds and a separator bottoms stream comprising $C_4$ hydrocarbons. The refrigerant stream, after contact with the gaseous effluent stream, undergoes compression followed by cooling with a desorption stream that cools the refrigerant while heating the desorption stream. The heated desorption stream contacts the adsorbent containing the additive at the desorption conditions to desorb the additive material from the adsorbent and produce an additive stream comprising hydrocarbons and the additive material. At least a portion of the additive stream passes to the reaction zone.

In a more limited embodiment, this invention is a process for the isomerization of a hydrocarbon stream containing $C_4$ hydrocarbons with a chloride promoted catalyst. The process comprises contacting a first stream comprising $C_4$ hydrocarbons with a chloride promoted catalyst in an isomerization reaction zone at isomerization conditions to convert normal hydrocarbons to branched hydrocarbons and produce an isomerization zone effluent stream comprising $C_3$ and $C_4$ hydrocarbons and a chloride compound. Separation of the isomerization zone effluent stream produces a liquid phase and a gaseous phase containing $C_3$ hydrocarbons, $C_4$ hydrocarbons, and a chloride compound. A gaseous input stream comprising at least a portion of the gaseous phase passes to an adsorption zone containing an adsorbent having adsorption capacity for the adsorption of the chloride compound and contacts the gaseous input stream with the adsorbent at adsorbent conditions to adsorb the chloride compound on the adsorbent and produce a gaseous effluent stream having a reduced concentration of the chloride compound relative to the gaseous input stream and an adsorbent loaded with the chloride compound. Indirect heat exchange with at least a portion of a refrigerant stream chills at least a portion of the gaseous effluent stream to produce a chilled gaseous effluent stream. The chilled gaseous effluent stream is separated into a light gas stream comprising $C_3$ hydrocarbons and a separator bottoms stream comprising $C_4$ hydrocarbons. The refrigerant stream undergoes compression and indirect contact with the desorption stream comprising $C_4$ hydrocarbons to cool the compressed refrigerant and heat the desorption stream. At least a portion of the heated desorption stream contacts the adsorbent containing the chloride compounds at desorption conditions to desorb chloride compounds from the adsorbent and to produce an additive stream comprising the chloride compounds. At least a portion of the additive stream passes to the isomerization reaction zone.

Additional details, embodiments and advantages of this invention are disclosed in the following detailed description of the preferred embodiments.

DETAILED DESCRIPTION OF THE PREFERRED EMBODIMENTS

A preferred embodiment of this invention is in the isomerization of $C_4$–$C_6$ hydrocarbons. The products of isomerization processes contribute to a gasoline blending pool. Such gasoline blending pools normally include $C_4$ and heavier hydrocarbons having boiling points of less than 205° C. (395° F.) at atmospheric pressure. This range of hydrocarbon includes $C_4$–$C_7$ paraffins and especially the $C_5$ and $C_6$ normal paraffins which have relatively low octane numbers. The $C_4$–$C_6$ hydrocarbons have the greatest susceptibility to octane improvement by lead addition and were formerly upgraded in this manner. Octane improvement is now often obtained by using isomerization to rearrange the structure of the straight-chain paraffinic hydrocarbons into branch-chained paraffins.

Preferred feedstocks are rich in normal paraffins having from 4 to 6 carbon atoms or a mixture of such substantially pure normal paraffins. The term "rich" is defined to mean a stream having more than 50% of the mentioned component. Other useful feedstocks include light natural gasoline, light straight run naphtha, gas oil condensate, light raffinates, light reformate, light hydrocarbons and straight run distillates having distillation end points of about 77° C. (170° F.) and containing substantial quantities of $C_4$–$C_6$ paraffins. Preferred isomerization feeds will consist mainly of $C_4$ hydrocarbons. The feedstream may also contain low concentrations of unsaturated hydrocarbons and hydrocarbons having more than 7 carbon atoms. The concentration of these materials should be limited to 10 wt. % for unsaturated compounds and 20 wt.% for heavier hydrocarbons in order to restrict hydrogen consumption and cracking reactions.

The isomerization of paraffins is generally considered a reversible first order reaction. The reaction is limited by thermodynamic equilibrium. The most common types of catalyst systems that are used in effecting the reaction are hydrochloric acid promoted aluminum chloride systems and supported aluminum chloride catalysts. The isomerization reaction zone typically contains a fixed bed of a chloride promoted isomerization catalyst. In the expectation that the feedstock will contain some olefins and, therefore, will undergo at least some cracking, the catalyst is preferably combined with an additional catalyst component that will provide a hydrogenation-dehydrogenation function. Preferably, this component is a noble metal of Group VIII of the periodic classification of the elements which are defined to include ruthenium, rhodium, platinum, osmium, iridium and palladium, with these specific metals being also known as the platinum group metals. The catalyst composition can be used alone or can be combined with a porous inorganic oxide diluent as a binder material. Other suitable binders include alumino-silicate clays such as kaolin, attapulgite, sepiolite, palygorskite, bentonite and montmorillonite, when rendered in a pliant plastic-like condition by intimate admixture with water, particularly when the clays have not been acid washed to remove substantial quantities of alumina.

Of these chlorided catalyst systems a particularly preferred type of catalyst consists of a high chloride catalyst on an alumina base containing platinum. The alumina may be selected from various forms including an anhydrous gamma-alumina with a high degree of purity. The catalyst may also contain other platinum group metals. These metals demonstrate differences in activity and selectivity such that platinum is the preferred metal for use in such catalysts. The catalyst will contain from about 0.1–0.25 wt. % platinum. Other platinum group metals may be present in a concentration from 0.1–0.25 wt. %. The platinum component may exist within the final catalytic composite as an oxide or halide or as an elemental metal. The presence of the platinum component in its reduced state has been found most suitable for this purpose. The catalyst also contains the chloride component. The chloride component termed in the art "a combined chloride" is present in an amount from about 2 to about 10 wt. % based upon the dry support material. The use of chloride in amounts greater than 5 wt. % have been found to be the most beneficial in these catalysts.

There are a variety of ways for preparing a chlorided catalytic composite and incorporating a platinum metal and chloride therein. The method that has shown the best results impregnates the carrier material through contact with an aqueous solution of a water-soluble decomposable compound of the platinum group metal. For best results, the impregnation is carried out by dipping the carrier material in a solution of chloroplatinic acid. Additional solutions that may be used include ammonium chloroplatinate, bromoplatinic acid or platinum dichloride. Use of the platinum chloride compound serves the dual function of incorporating the platinum component and at least a minor quantity of the chloride into the catalyst. Additional amounts of the chloride must be incorporated into the catalyst by the addition or formation of aluminum chloride to or on the platinum-alumina catalyst base. An alternate method of increasing the chloride concentration in the final catalyst composite is to use an aluminum hydrosol to form the alumina carrier material such that the carrier material also contains at least a portion of the chloride. Chloride may also be added to the carrier material by contacting the calcined carrier material with an aqueous solution of the chloride such as hydrogen chloride.

Again, it is generally known that high chlorided platinum-alumina catalysts of this type are highly sensitive to sulfur and oxygen-containing compounds. A sulfur concentration of 0.5 ppm in the feed or less is required, since the presence of sulfur in the feedstock serves to temporarily deactivate the catalyst by platinum poisoning. Activity of the catalyst may be restored by hot hydrogen stripping of sulfur from the catalyst composite or by lowering the sulfur concentration in the incoming feed to below 0.5 ppm so that the hydrocarbon will desorb the sulfur that has been adsorbed on the catalyst. Water and oxygenate compounds are generally kept to a concentration of 0.1 ppm or less. The more stringent limitation on water and oxygenate compounds that decompose to form water stems from the fact that water can act to permanently deactivate the catalyst by removing high activity chloride from the catalyst and replacing it with inactive aluminum hydroxide.

Although sulfur compounds will not cause permanent deactivation, isomerization feeds will usually contain sulfur which will interfere with the isomerization operations. Sulfur contaminants are present with the original crude oil fraction and include mercaptans, sulfides, disulfides and thiophenes. For light straight run feeds, sulfur concentrations will usually range from 20-300 ppm. Rapid coking of the catalyst has been experienced in most cases following sulfur deactivation. If left unchecked, the coking will be severe enough to require a complete regeneration of the catalyst. Therefore, it is common practice to minimize the amount of sulfur that contacts catalyst in the isomerization zone to prevent deactivation and avoid a full regeneration of the catalyst.

When a chlorided catalyst is used, operation of the isomerization zones often uses a small amount of a chloride promoter. The chloride promoter, typically an organic chloride serves to maintain a high level of active chloride on the catalyst as low levels are continuously stripped off the catalyst by the hydrocarbon feed. The concentration of promoter in the reaction zone is preferably maintained at 30–300 ppm. The preferred promoter compound is perchloroethylene. Other suitable promoter compounds include oxygen-free decomposable organic chlorides such as propyldichloride, butylchloride, and chloroform to name only a few of such compounds. The need to keep the reactants dry is reinforced by the presence of the organic chloride compound which may convert, in part, to hydrogen chloride. As long as the process streams are kept dry, there will be no adverse effect from the presence of small amounts of hydrogen chloride.

These chloride promoted catalysts are very reactive and can generate undesirable side reactions such as disproportionation and cracking. These side reactions not only decrease the product yield but can form olefinic fragments that polymerize or deposit on the catalyst and shorten its life. One commonly practiced method of controlling these undesired reactions has been to carry out the reaction in the presence of hydrogen.

When contacting the catalyst in the isomerization reaction zone, the feed is heated as necessary to achieve the desired reaction temperature and then enters the isomerization reaction zone. Operating conditions within the isomerization zone are selected to maximize the production of isoalkane product from the feed components and are influenced by the type of catalyst as well as the composition of the feed. Two reaction zones are typically provided due to a temperature rise that initially occurs from hydrogenation reactions. Conditions within the first isomerization zone typically include a temperature in the range of 190°–290° C. (375°–550° F.), a pressure from 1200–3100 kPag (175–450 psig) and a liquid hourly space velocity from 4–20 hr$^{-1}$. Typically, the reaction conditions are selected to keep the hydrocarbon feed in a vapor or mixed phase. Temperatures within the second conversion zone will usually operate at somewhat lower temperatures and range from about 65°–280° C. (150°–536° F.). These lower temperatures are particularly useful in processing feeds composed of $C_5$ and $C_6$ paraffins where the lower temperatures favor equilibrium mixtures having the highest concentration of the most branched paraffins. When the feed mixture is primarily $C_5$. and $C_6$ paraffins, temperatures in the range of 65°–160° C. (150°–320° F.) are preferred. When it is desired to isomerize significant amounts of $C_4$ hydrocarbons, higher reaction temperatures are required to maintain catalyst activity. Thus, when the feed mixture contains significant portions of $C_4$–$C_6$ paraffins most suitable operating temperatures are in the range from 140°–235° C. (280°–455° F.). The second conversion zone may be maintained over the same range of pressures given for the first conversion zone. The feed rate to the second conversion zone may also vary over a wide range but will usually include liquid hourly space velocities that are lower than the first conversion zone and range from 0.5–12 hr.$^{-1}$, with space velocities between 1 and 8 hr.$^{-1}$ being preferred. The hydrogen concentration in the second conversion zone may also be adjusted by the addition of hydrogen to the feed or to the second conversion zone. The particular operating conditions within the isomerization zone will also be influenced by the makeup of the feedstream and the catalyst composition employed therein.

Whether operating with one or more reactors the effluent from the isomerization zone will enter a separation zone for the removal of light gases from the isoparaffin containing product stream. The light gases typically include hydrogen added to the feedstream entering the first conversion zone and any additional hydrogen that was added to the feed entering the second conversion zone. At minimum, the separation facilities divide the conversion zone effluent into a product stream comprising $C_4$ and heavier hydrocarbons and a gas stream which is made up primarily of lighter hydrocarbons and hydrogen, but will usually also contain recoverable $C_4$. Suitable designs for rectification columns and separator vessels are well known to those skilled in the art. The separation section may also include facilities for recovery of normal alkanes. Normal alkanes recovered from the separation facilities may be recycled to either the first or second conversion zone to increase the conversion of normal alkanes to isoalkanes.

In accordance with this invention, an adsorption zone recovers the chloride that the feed strips from the isomerization catalyst. Therefore, at least a portion of the effluent from the reaction zone contacts an adsorbent having a capacity for chloride compounds. Unless otherwise noted the term "portion" in this specification when describing a process stream refers to either an aliquot portion of the stream or a dissimilar fraction of the stream having a different composition than the total stream from which it was derived. The process may be arranged such that the adsorption zone receives the entire effluent from the isomerization zone. However, most of the chloride compounds are ordinarily contained in the light gas stream from overhead of the stabilizer vessel that removes most of the $C_3$ hydrocarbons and the lighter gases.

In the preferred form of this invention the $C_3$ and lighter hydrocarbon stream, which will include recoverable $C_4$ hydrocarbons, and any excess hydrogen from the second conversion zone are passed first to an adsorption zone for the removal of chloride compounds before entering a hydrocarbon recovery section. The adsorption step of this process can be implemented with many different adsorbents such as zeolites, clays, inorganic polymers such as activated alumina, silica gel, zirconia, carbon, organic polymers such as resin adsorbent, etc. Not as a limitation on the scope of the process of this invention, but as a further discovery of preferred adsorbents, it has been found that ion-exchanged clinoptilolites particularly, NaK clinoptilolite, acid washed Ba clinoptilolite, MgK clinoptilolite, acid leached clinoptilolite, $NH_4$ clinoptilolite, etc. are particularly suitable for recycling HCl. Clinoptilolite as an adsorbent with adjustable pore size and acid resistance is described in U.S. Pat. No. 4,935,580 issued to Chao et al., U.S. Pat. No. 4,964,889 issued to Chao, and U.S. Pat. No. 5,164,076 issued to Zarchy, Chao and Correia, the contents of which are hereby incorporated by reference. For NaK and MgK clinoptilolite, the preferred concentration of potassium ions is in the range of 15 to 75%, and more preferably in a range of 30 to 70%, and the concentration of Na and Mg are preferably in a range of 25 to 85% and more preferably in a range of 30 to 70%. The sum of Na and K or Mg and K are in the range of 50 to 100% of the total ion exchange capacity of the adsorbent. For Ba clinoptilolite, the barium concentration should be in the range of 20 to 100% of the ion exchange capacity. Other useful compositions include K, Na, Li, H, Mg, Ca, Sr, Zn, Mn, Co, CaK, SrK, ZnK, MnK, CoK and BaK cation exchanged or naturally occurring clinoptilolites and their acid washed version with the intended cations accounting for 50 to 100% of the total ion-exchange capacity of the clinoptilolite. Additional information for the selection and preparation of suitable clinoptilolite adsorbents can be found in U.S. Pat. No. 5,238,555, the contents of which are hereby incorporated by reference.

The product hydrocarbons will include at least $C_3$ and $C_4$ hydrocarbons. As stated earlier with respect to the feed the product hydrocarbons may also include $C_5$ through $C_7$ and heavier hydrocarbons. The product stream will also usually include hydrogen. In addition to hydrogen, the lighter gases present with the effluent stream usually include ethane and propane which are often by-products produced by catalytic hydrocarbon conversion processes. The adsorbent should have a low capacity for these other hydrocarbon components. NaK clino, acid washed Ba clinoptilolite, and MgK clinoptilolite, as previously described, have suitably low capacity for $C_3$ and lighter hydrocarbons and are preferred adsorbents. Acid washed clinoptilolite has a somewhat higher $C_3$ capacity and is less preferred.

A fixed bed retains the adsorbent in the adsorption zone for contact with the input and effluent streams from the reaction zone. The adsorption zone preferably contains two or more adsorbent beds to continuously adsorb and desorb material from the effluent and the input stream. Typical conditions for operation of the adsorbent zones will again depend upon the particular adsorbents used and the temperature and pressure conditions of the inlet and effluent stream from the reaction zone. Typical conditions will include temperatures from 50°–750° F. and pressures of from 1 atmosphere to 50 atmospheres and the feedstream can contact the adsorbent in vapor or liquid phase conditions. Adsorbents should be selected to correspond with the temperature conditions of the effluent or effluent portion that enters the adsorption section. Preferably, the processing conditions will maintain the feedstream through the adsorption zone in a vapor phase.

The type of separation zone and the hydrogen concentration in the effluent will influence the placement and operation of the adsorption zone for the recovery of chloride compounds. Traditional isomerization processes operated with a relatively high recycle of hydrogen. In order to conserve hydrogen and stabilize the effluent, the effluent from the isomerization zone will pass directly to a hydrogen separator when the hydrogen to hydrocarbon ratio exceeds about 0.05. Cooling ahead of the hydrogen separator will lower the remainder of the effluent stream to a temperature in a range of from 80°–140° F. Thus, the temperature condition of the effluent leaving the hydrogen separator is suitable for adsorption of chloride compounds. Where there is a hydrogen recycle, the chloride adsorber bed undergoing the adsorption step may receive the effluent stream passing from the hydrogen separator to a stabilizer for the separation of isomerate product from non-condensibles or in accordance with the preferred embodiment of this invention the adsorption zone will receive the non-condensible stream from the stabilizer. Isomerization zone processes that operate with very low hydrogen concentrations in the feed and the effluent eliminate the hydrogen separator and any accompanying recycle compressor to reduce utility and capital cost. In these cases, the effluent stream passes directly from the isomerization reaction zone to the stabilizer. In most cases, the temperature of the effluent passing from the isomerization reaction zone to the stabilizer exceeds a suitable adsorption temperature. Therefore, where the isomerization reaction zone operates without hydrogen recycle, the chloride adsorber generally adsorbs chloride compounds from the overhead of the stabilizer. Since most of the chloride compounds are contained in the stabilizer overhead, the isomerate from the stabilizer is still relatively free of chloride compounds and a majority of the chlorides are recovered for return to the isomerization reaction zone.

After removal of the chloride compound and separation of most $C_4$ and heavier hydrocarbons at least an aliquot portion of the remainder of the effluent stream undergoes chilling for the further recovery of $C_4$ hydrocarbons. This invention provides the chilling with a refrigeration arrangement that uses a desorption stream to at least partially condense the refrigerant. In regard to refrigeration, any suitable refrigeration means may be employed as long as the desorption stream provides a suitable condensing stream. For example, a simple cycle comprising a refrigerant evaporator, compressor, condenser, and expansion valve may be employed. If desired, the refrigeration operation may employ a more complex cascade system. The exact nature and configuration of the refrigeration scheme is dependent on the desired temperature of the refrigerated admixture and in turn that temperature is dependent on the composition of the admixture and the desired degree of recovery of $C_4$ hydrocarbons.

Since the isomerization effluent is usually dry, ice formation in the refrigeration heat exchange section will not ordinarily present problems. In a typical arrangement the stabilizer overhead is essentially dry.

Preferably the chloride deficient gas stream from the stabilizer will undergo chilling to a temperature that maximizes the recovery of hydrocarbon products from lighter gas components. In order to achieve the most advantageous temperature from the chilling operations, this stabilizer offgas stream may undergo additional stages of heat exchange upstream of the chiller. Preferably, the refrigerated temperature should be as low as possible with some margin of safety to prevent freezing. Generally, the refrigerant will cool a portion of the effluent stream to a temperature from about $-20°$ to $+40°$ F.

After chilling, the chilled offgas enters a chiller separator for removal of light gas components from the product stream. Products recovered by the separator will normally include $C_4$ hydrocarbons which, in the case of isomerization, are returned to the stabilizer for recovery with a main product stream. Product hydrocarbons recovered after chilling may still contain small quantities of $C_3$ hydrocarbons. The temperature of the chilled offgas stream may be adjusted to maintain the amount of $C_3$ hydrocarbons in the product stream at a suitable level.

It is also possible to incorporate an additional adsorption medium such as a sponge oil into the stabilizer offgas stream in order to maximize the recovery of product hydrocarbons. While the use of such additional absorption mediums may provide some benefits, in most cases suitable recoveries can be obtained without their use.

The remaining portion of the offgas stream from the chiller separator may contain relatively high quantities of hydrogen which are worth recovering by an additional step of chilling. Any suitable method may be used to further chill the separator offgas stream to separate $C_1$ and $C_2$ non-condensibles from the hydrocarbon stream and thereby provide a high purity hydrogen stream. Where the chiller separator offgases are chilled for further recovery of hydrogen, the second chiller will usually reduce the temperature of the offgas stream to a range from $0°$ to $-60°$ F. In a preferred form of this invention, a high purity hydrogen stream is recovered by further contact of the separator offgas stream in an additional chiller that receives a portion of the cooled refrigerant from a common refrigeration zone. Thus, the refrigerant is sent to two chillers which can be back pressure controlled to maintain separate operating temperatures in the two chillers. In such an arrangement, the first chiller is operated to reclaim the maximum amount of hydrocarbon product material while the second chiller is operated to achieve a desired hydrogen recovery and hydrogen purity. Where the refrigerant is sent to both chiller exchangers, the same adsorbent stream can be used for the refrigerant condenser. After chilling, the separator offgas stream enters an additional hydrogen separator that provides a high purity hydrogen stream as an overhead. The overhead hydrogen stream may be recycled back to the isomerization zone as make up hydrogen. The bottoms stream from the hydrogen separator is usually used as a fuel gas stream.

Again any suitable refrigeration means may be employed for the recovery of hydrogen. The exact nature and configuration of the refrigeration scheme is dependent on the desired temperature of the refrigerated admixture and in turn that temperature is dependent on the composition of the admixture and the desired hydrogen purity of the hydrogen-rich gas. Preferably, the temperature should be as low as possible with some margin of safety to prevent freezing.

The hydrogen-rich gas stream withdrawn from the absorption zone will preferably have, depending on the conditions therein, a hydrogen purity in excess of 90 mol. %. After subjecting the hydrogen-rich gas stream to indirect heat exchange pursuant to the invention, the hydrogen-rich gas stream may then be passed to other hydrogen-consuming processes or may be utilized in any suitable fashion.

The gas separation steps of this invention will employ chilling step. The desorption stream of this invention provides two functions by condensing the refrigerant for the chilling step and desorbing chloride compounds from the adsorption zone during the desorption step. The desorption stream may be a fraction of any stream that normally enters the reaction zone.

In a typical $C_4$ isomerization process, the desorption stream will be a fraction of the $C_4$ feed. The amount of feed liquid needed for desorbing chloride compounds from the adsorber beds is generally less than 5% of the total feed volume entering the process and, more typically less than 3% of the total feed volume. The $C_4$ fraction will first pass through a condensing exchanger to condense the refrigerant. Passage through the condensing exchanger will heat the $C_4$ stream from a temperature of about 85 to 110° F. to a temperature of about 140° to 200° F. As the desorbtion stream cools the refrigerant, it picks up heat.

Typically, additional heating superheats the desorption stream to permit desorption of hydrogen chloride from the adsorbent in the adsorption zone. The desorption stream desorbs chloride compounds from an adsorbent bed that previously contacted the stabilizer offgas stream and adsorbed chloride compounds therefrom. Contact of the chloride loaded bed desorbs the chloride compounds from the adsorbent bed. At least a portion of the desorbent stream containing the chloride compounds is returned to the reactor vessel. In most cases the desorbent stream, which is still in vapor phase when leaving the adsorption zone, undergoes condensing for return to the isomerization reaction zone.

Figure 1:
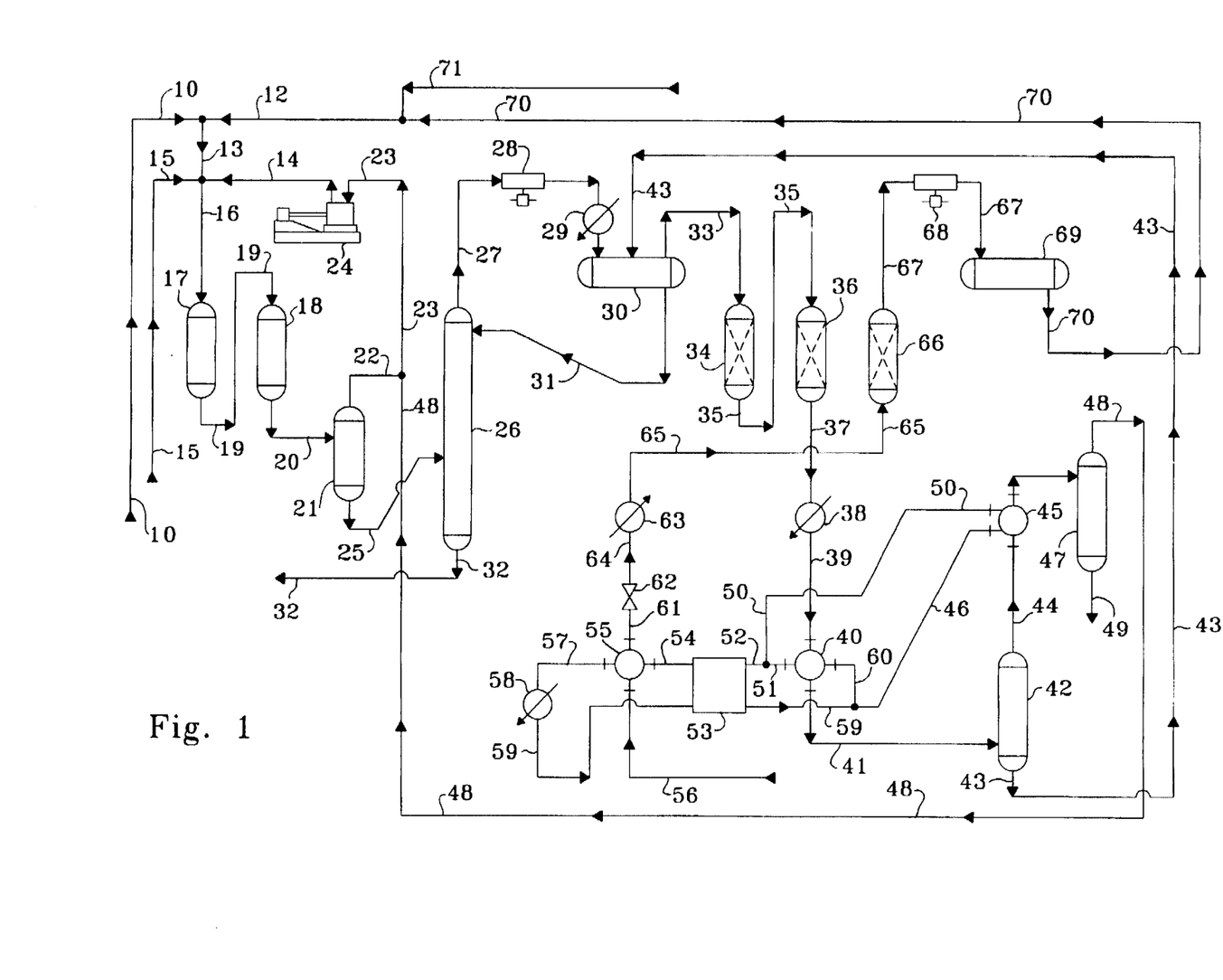
FIG. 1 is a schematic flow diagram that illustrates a simplified isomerization zone embodiment of FIG. 1 and includes steps for hydrogen recovery and recycle.

In order to demonstrate the operation of this invention, an isomerization reaction zone arrangement that uses a chlorided platinum alumina catalyst and operated with a recycle of hydrogen is depicted in FIG. 1. FIG. 1 is a schematic representation of the process and shows only the portions of the major equipment necessary to carry out the process. Other related equipment such as separators, pumps, compressors, etc. are well known to those skilled in the art and are not necessary for an understanding of Applicant's invention or the underlying concepts.

In the isomerization process of FIG. 1, a hydrocarbon feedstream containing 4 to 7 carbon atoms and derived from a light naphtha feedstream enters the process through line 10. A recycle stream of $C_4$ hydrocarbons carried by line 12 is combined with the feed in line 13. The feed in line 13 mixes with a make-up hydrogen stream carried by line 15 and a recycle stream of light gases carried by line 14 and comprising at least 50 wt. % hydrogen. Preferably, the hydrogen-containing gas stream will have a hydrogen concentration greater than 75 wt. % hydrogen. The hydrogen containing gas stream and the isomerization feed are taken by line 16 and in proportions that produce a molar hydrogen to hydrocarbon ratio from 0.5 to 2. Line 16 carries the feed mixture through one or more heating and heat exchange steps (not shown) and delivers the feed to a series of reactors 17 and 18, connected by line 19. The isomerization reactor vessels 17 and 18 contain chlorided platinum alumina catalyst that contacts the feedstream and produces an isomerization zone product stream.

Line 20 carries the effluent from isomerization zone 18 to stages of separation, desorption and adsorption. After heat exchange and cooling (not shown) the effluent from the reaction zone enters a separator 21 for the separation of hydrogen from the isomerization effluent. A hydrogen containing stream is taken overhead from separator 21 by line 22 and recycled to the reaction zone via line 23 and compressor 24. Line 25 carries the remainder of the isomerization zone effluent stream to a stabilizer 26 that separates lighter hydrocarbons and gases from the heavier hydrocarbons of the entering effluent stream. Line 27 recovers $C_3$ and lighter hydrocarbons overhead and passes the recovered light gases through a condenser 28, a cooler 29, and into an overhead drum 30. Line 31 carries condensed liquid from drum 30 back to stabilizer 26 as a reflux stream. Hydrocarbon liquid comprising the main product stream from the isomerization zone exits the bottom of the stabilizer vessel through line 32.

$C_3$ and lighter hydrocarbons, hydrogen, other non-condensible gases, and some $C_4$ and heavier hydrocarbons are carried overhead from reflux drum 30 via line 33 and into a series of adsorber vessels 34 and 36. Adsorber vessels 34 and 36 contain an adsorbent having a capacity and selectivity for chlorides along with a resistance to the corrosive effects of the chloride compounds. Line 35 connects adsorber vessels 34 and 36 which operate in a lead and trim configuration such that the upstream adsorber vessel continues to receive the chloride containing overhead until such time as the adsorbent becomes fully loaded with chloride compounds while the downstream adsorber adsorbs chloride compounds from any disequilibrium front that may pass through the upstream adsorber as it reaches full capacity. Once fully loaded the former downstream adsorber vessel begins to initially receive the overhead stream while the former upstream vessel undergoes regeneration to desorb chloride compounds and a vessel containing regenerated adsorbent replaces the downstream adsorber vessel.

Line 37 carries a substantially chloride-free stream from adsorber vessel 36 that is further processed for the recovery of $C_4$ hydrocarbons and gaseous components in accordance with this invention. The now chloride-free overhead stream from the stabilizer passes first through a cooler 38 that reduces its temperature and then passes via line 39 to a chiller 40. Chiller 40 indirectly contacts the stabilizer overhead with a refrigerant to condense $C_4$ and heavier hydrocarbons which are carried via a line 41 to a chiller separator 42. Line 43 returns $C_4$ and heavier hydrocarbons to overhead drum 30 for return to stabilizer 26 and recovery of $C_4$ products in the main product stream 32. The remaining $C_3$ and lighter hydrocarbons and hydrogen are taken overhead from separator 42 via line 44 and again chilled in a chiller 45 by indirect heat exchange with a portion of a refrigerant stream carried by line 46. The chilled hydrogen containing stream enters a hydrogen separator 47 that provides a purified hydrogen stream taken overhead by line 48 and a bottoms fuel gas stream 49. Line 48 returns the purified hydrogen stream to the recycle hydrogen compressor 24 via line 23.

Line 50 returns refrigerant from chiller 45 and mixes it with refrigerant from chiller 40 carried by line 51. Line 52 returns the mixture of heated refrigerant to a refrigeration zone 53. Refrigeration zone 53 compresses the heated refrigerant which passes via line 54 into an exchanger 55 and into indirect heat exchange with a desorbent stream 56. Desorbent stream 56 partially cools the refrigerant which passes via line 57 to a trim cooler 58. Cooled refrigerant from trim cooler 58 passes via line 59 to lines 60 and 46 which supply refrigerant to chillers 40 and 45.

Desorbent stream 56 contains $C_4$ hydrocarbons which comprise a portion of the feed to the isomerization reactors. Line 61 delivers the heated desorbent stream from refrigerant condenser 55 through an expansion valve 62 that partially vaporizes the desorption stream prior to its passage through a super heater 63 via a line 64. Expansion valve 62 or other similar device could be located upstream of condenser 55 to achieve partial vaporization in condenser 55. Line 65 passes the super heated desorption stream into an adsorber vessel 66 that is fully loaded with chloride compounds and undergoing desorption. Line 67 carries desorbed chloride compounds in admixture with the $C_4$ feed components through a condenser 68 and into an overhead drum 69. The returning desorption fluid in line 67 undergoes cooling in order to prevent flashing and loss of potential feed in a feed drum which is ordinarily provided for supplying feed to the reactors (not shown). (Variations in the level of the feed drum are accommodated by venting gas from the feed drum. This arrangement for venting the feed drum could cause excessive flashing of hydrocarbons if the hot desorption stream directly enters the feed drum.) The chloride containing feed fraction from drum 69 returns to the isomerization zone via line 70 where necessary make-up chloride enters line 70 via line 71.

The chloride-containing desorption fluid becomes part of the feed mixture that passes to the isomerization reactor. Desorption fluid passing through line 70 will supply the majority of the chloride needed for the promotion of the isomerization catalyst in reactors 17 and 18. To make up for any small chloride losses, additional chloride compound is added upstream of reactor 17 via line 71.

To more fully demonstrate the attendant advantages of the present invention, the following examples, based on thermodynamic analysis, engineering calculations, and estimates are set forth. Details such as miscellaneous pumps, heaters, coolers, valving, start-up lines, and similar hardware have been omitted as being non-essential to a clear understanding of the techniques involved.

Figure 2:
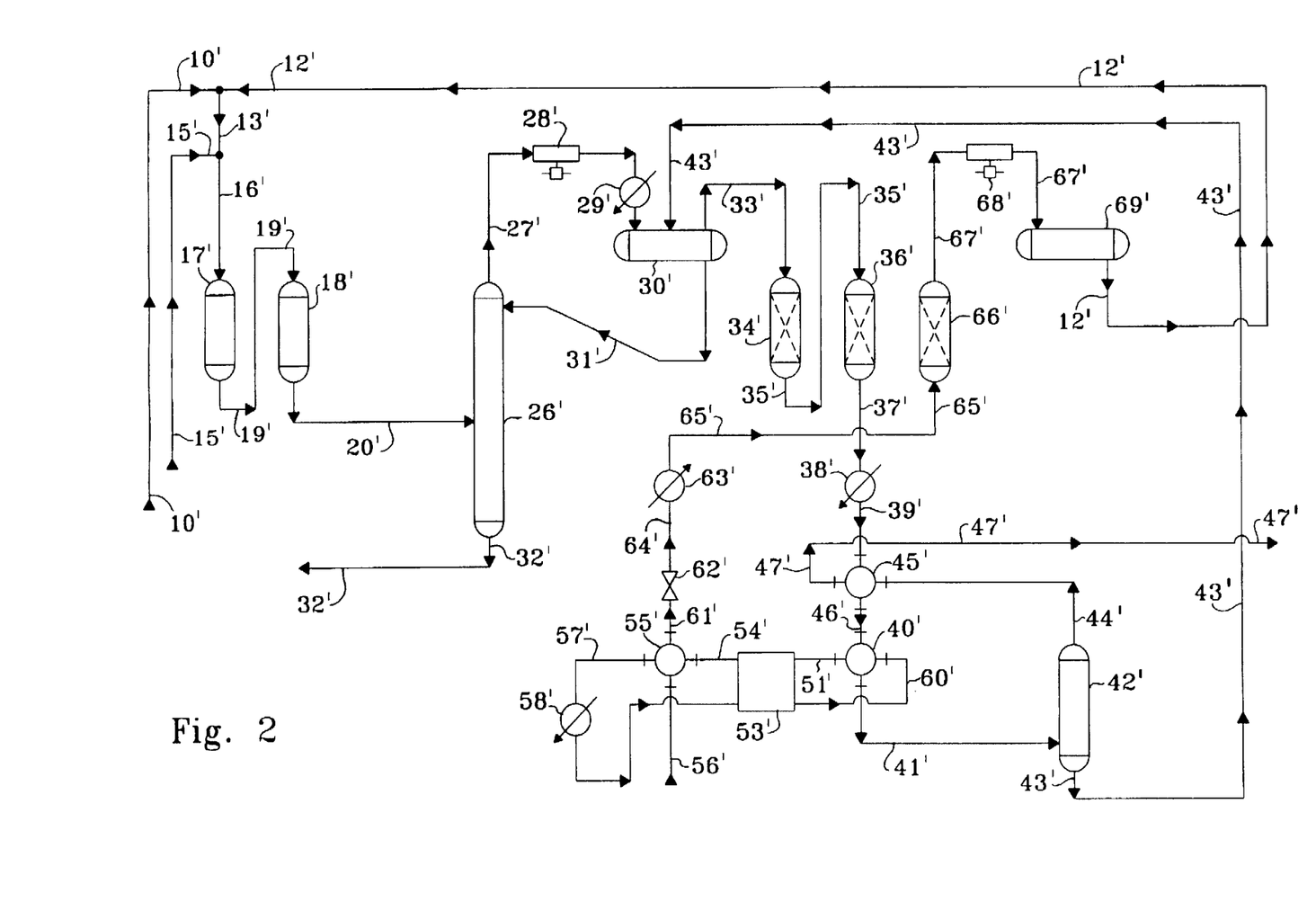
FIG. 2 is a schematic flow diagram that illustrates a simplified isomerization zone embodiment of this invention without hydrogen recycle.

FIG. 2 exemplifies another operation of this invention wherein the process uses a low hydrogen concentration to provide a once-through utilization of hydrogen. Suitable processes for this type of operation will usually produce isomerization zone effluents having hydrogen to hydrocarbon molar ratios of 0.05 or less.

The arrangement of this operation is similar to that depicted in FIG. 1 except for the absence of any hydrogen recycle and recovery steps. Thus referring to FIG. 2 a feedstream fraction having the composition given in the table for line 12' is admixed with a primary feedstream 10' to produce an isomerization zone feed taken via line 13' and admixed with hydrogen from line 15' to produce an isomerization zone feed. Lines 16' and 19' carry the isomerization zone feed through a series of reactors 17' and 18' that contain a chlorided platinum aluminum catalyst at conditions that produce a reactor effluent stream having the composition given for line 20' in the table and a hydrogen to hydrocarbon ratio of less than 0.05.

TABLE

| COMPONENT | 12' | 20' | 32' | 33' | 43' | 47' | 56' |
|---|---|---|---|---|---|---|---|
| $H_2$ | 0.05 | 29.81 | 0.00 | 30.09 | 0.28 | 29.81 | 0.05 |
| $C_1$ | 0.00 | 7.66 | 0.00 | 8.52 | 0.86 | 7.66 | 0.00 |
| $C_2$ | 0.00 | 5.52 | 0.00 | 9.03 | 3.52 | 5.51 | 0.00 |
| $C_3$ | 0.00 | 5.33 | 2.69 | 9.42 | 6.78 | 2.64 | 0.00 |
| $IC_4$ | 2.32 | 658.05 | 656.30 | 14.12 | 12.37 | 1.74 | 2.32 |
| $NC_4$ | 17.11 | 517.23 | 517.11 | 1.38 | 1.27 | 0.12 | 17.11 |
| $IC_5$ | 0.35 | 25.05 | 25.05 | 0.00 | 0.00 | 0.00 | 0.35 |
| $NC_5$ | 0.18 | 16.70 | 16.70 | 0.00 | 0.00 | 0.00 | 0.18 |
| HCL | 0.30 | 0.00 | 0.00 | 0.30 | 0.00 | 0.00 | 0.00 |

The reactor effluent enters a stabilizer 26' at a temperature of about 225° F. and a pressure of about 435 psig. Stabilizer 26' separates a bottoms product stream having the composition given in the table for line 32'. Line 27' carries the overhead from the stabilizer through a condenser 28' and a cooler 29' into an overhead drum 30'. After the addition of recycled $C_4$ product via line 43' and the reflux of condensed overhead material via line 31', a net overhead stream having the composition given in the table for line 33' is withdrawn.

The net overhead stream 33' passes through a series of adsorption vessels containing an adsorbent selected for the removal of chloride compounds from the overhead stream. Passage through this series of adsorbers 34' and 36' via line 35' produces an essentially chloride-free net overhead stream that is removed from the adsorbent vessels via line 37' and cooled to a temperature of about 100° F. by a cooler 38'. Line 39' passes the cooled chloride-free overhead in indirect heat exchange against a separator overhead stream 44' in a heat exchanger 45'. Passage of the cooled overhead vapors via line 46' through chiller 40' chills the overhead stream to a temperature of about 10° F. The chilled overhead stream passes at a pressure of about 258 psig via line 41' to a separator 42'. This separator produces a hydrogen-containing stream suitable for fuel gas use having a composition given under the line 47' in the table. Line 43' returns the separator bottoms to the stabilizer drum 30'. The bottoms of separator 42' has the composition given in the table for line 43'.

Heated refrigerant from chiller 40' passes via line 51' into a refrigeration section 53' that compresses the refrigerant and passes it via line 54' for condensing in a heat exchanger 55' against a desorbent stream 56' which has the composition given in the table. Line 57' delivers the condensed refrigerant to an exchanger 58' for further cooling and contact with the adsorbent overhead stream via line 60'. Contact with the refrigerant heats the desorbent stream 56' from a temperature of about 100° F. to a temperature of about 180° F. Line 61' carries the heated desorbent through an expansion valve 62' and into a super heater 63' via line 64'. Line 65' carries the super heated desorption stream having a temperature of about 350° F. into contact with chloride-containing adsorbent in an adsorbent vessel 66'. Line 67' carries the desorbent stream through a condenser 68' such that a desorbent surge drum 69' recovers the chloride-containing desorbent at a temperature of about 120° F. and a pressure of about 112 psig.

As shown by the composition of stream 12', the adsorber arrangement recovers essentially all of the hydrogen chloride present in the feedstream which is returned to the isomerization reactors via line 12' as previously described.

We claim:

1. A process for recovering $C_4$ and heavier hydrocarbons from the effluent of a catalytic hydrocarbon conversion process that employs a mobile additive in a reaction zone and produces an effluent comprising $C_4$ hydrocarbons and $C_3$ and lighter hydrocarbons, said process comprises the steps of:
   (a) contacting a first stream comprising hydrocarbons with a catalyst in a reaction zone in the presence of said additive material at hydrocarbon conversion conditions to convert hydrocarbons and produce a second stream comprising $C_4$ hydrocarbons, $C_3$ hydrocarbons and said additive material;
   (b) separating said second stream into a liquid phase and into a gaseous phase comprising $C_4$ hydrocarbons, $C_3$ hydrocarbons and said additive material;
   (c) passing a gaseous input stream comprising at least a portion of said gaseous phase to an adsorption zone containing an adsorbent having adsorption capacity for said additive material and contacting said gaseous input stream with said adsorbent at adsorption conditions, adsorbing said additive material on said adsorbent and producing a gaseous effluent stream having a reduced concentration of said additive material relative to said gaseous input stream and an adsorbent containing said additive material;
   (d) chilling at least a portion of said gaseous effluent stream by indirect heat exchange to a temperature of −20° to 40° F. with at least a portion of a refrigerant stream to produce a chilled gaseous effluent stream;
   (e) separating at least a portion of said chilled gaseous effluent into a light gas stream comprising $C_3$ hydrocarbons and lower boiling compounds and a separator bottoms stream comprising $C_4$ hydrocarbons;
   (f) compressing said refrigerant and indirectly contacting the compressed refrigerant with a desorption stream comprising hydrocarbons to cool said compressed refrigerant and heat said desorption stream and at least partially vaporizing the desorption stream;
   (g) contacting the heated desorption stream with said adsorbent containing said additive at desorption conditions to desorb said additive material from said adsorbent and to produce an additive stream comprising hydrocarbons and said additive; and,
   (h) passing at least a portion of said additive stream to said reaction zone.

2. The process of claim 1 wherein said additive comprises a chloride compound.

3. The process of claim 2 wherein said adsorbent is a clinoptilolite molecular sieve.

4. The process of claim 2 wherein said process is an isomerization process and said first stream comprises hydrocarbons having from 4 to 6 carbon atoms.

5. The process of claim 1 wherein said adsorption zone recovers at least 90 wt. % of said additive present in said second stream.

6. The process of claim 1 wherein said adsorption zone recovers at least 99 wt. % of said additive material from said gaseous input stream.

7. The process of claim 1 wherein said second stream includes hydrogen and said light gas stream is contacted with a portion of said refrigerant stream to chill said light gas stream and said light gas stream is separated into a purified hydrogen stream and a fuel gas stream.

8. A process for the isomerization of a hydrocarbon stream containing $C_4$ hydrocarbons with a chloride promoted catalyst, said process comprising:

(a) contacting a first stream comprising $C_4$ hydrocarbons with a chloride promoted catalyst in an isomerization reaction zone at isomerization conditions to convert normal hydrocarbons to branched hydrocarbons and produce an isomerization zone effluent stream comprising $C_3$ and $C_4$ hydrocarbons and a chloride compound;

(b) separating said isomerization zone effluent stream into a liquid phase and into a gaseous phase containing $C_3$ hydrocarbon, $C_4$ hydrocarbon and a chloride compound;

(c) passing a gaseous input stream comprising at least a portion of said gaseous phase to an adsorption zone containing an adsorbent having adsorption capacity for the adsorption of said chloride compound and contacting said gaseous input stream with said adsorbent at adsorption conditions, adsorbing said chloride compound on said adsorbent and producing a gaseous effluent stream having a reduced concentration of said chloride compound relative to said gaseous input stream and an adsorbent containing said chloride compound;

(d) chilling at least a portion of said gaseous effluent stream by indirect heat exchange to a temperature of $-20°$ to $40°$ F. with at least a portion of a refrigerant stream to produce a chilled gaseous effluent stream;

(e) separating at least a portion of said chilled gaseous effluent into a light gas stream comprising $C_3$ hydrocarbons and a separator bottoms stream comprising $C_4$ hydrocarbons;

(f) compressing said refrigerant stream and indirectly contacting the compressed refrigerant with a desorption stream comprising $C_4$ hydrocarbons to cool said compressed refrigerant and heat said desorption stream and at least partially vaporizing the desorption stream;

(g) contacting said adsorbent containing said chloride compounds at desorption conditions with at least a portion of the heated desorption stream to desorb chloride compounds from said adsorbent and to produce an additive stream comprising said chloride compounds; and, (h) passing at least a portion of said additive stream to said isomerization reaction zone.

9. The process of claim 8 wherein said adsorbent is a clinoptilolite molecular sieve.

10. The process of claim 8 wherein said first stream comprises hydrocarbons having from 4 to 6 carbon atoms.

11. The process of claim 8 wherein the adsorbent having capacity for a chloride compound is selected from the group consisting of Na and K, Mg and K and barium ion-exchanged clinoptilolite, silicalite and silicagel.

12. A process for the isomerization of a hydrocarbon stream containing $C_4$ hydrocarbons with a chloride promoted catalyst, said process comprising:

(a) contacting a first stream comprising $C_4$ hydrocarbons and hydrogen with a chloride promoted catalyst in an isomerization reaction zone at isomerization conditions to convert normal hydrocarbons to branched hydrocarbons and producing an isomerization zone effluent stream comprising $C_1$ to $C_4$ hydrocarbons, and hydrogen;

(b) separating said isomerization zone effluent stream into a liquid phase and into a gaseous phase containing $C_1$ to $C_4$ hydrocarbons and a chloride compound;

(c) passing a gaseous input stream comprising at least a portion of said gaseous phase to an adsorption zone containing an adsorbent having adsorption capacity for the adsorption of said chloride compound and contacting said gaseous input stream with said adsorbent at adsorption conditions, adsorbing said chloride compound on said adsorbent and producing a gaseous effluent stream having a reduced concentration of said chloride compound relative to said gaseous input stream and an adsorbent containing said chloride compound;

(d) chilling at least a portion of said gaseous effluent stream by indirect heat exchange with a first portion of a refrigerant stream to produce a chilled gaseous effluent stream;

(e) separating at least a portion of said chilled gaseous effluent into a light gas stream comprising $C_3$ through $C_1$ hydrocarbons and hydrogen and a separator bottoms stream comprising $C_4$ hydrocarbons;

(f) chilling at least a portion of said light gas stream by indirect heat exchange with a second portion of said refrigerant stream and separating said light gas stream into a purified hydrogen stream containing hydrogen and a noncondensible gas stream comprising $C_1$ through $C_3$ hydrocarbons;

(g) compressing said refrigerant stream and indirectly contacting the compressed refrigerant with a desorption stream comprising $C_4$ hydrocarbons to cool said compressed refrigerant, heat said desorption stream, and at least partially vaporize the desorption stream;

(h) contacting said adsorbent containing said chloride compounds at desorption conditions with at least a portion of the heated desorption stream to desorb chloride compounds from said adsorbent and to produce an additive stream comprising said chloride compounds; and, (i) passing at least a portion of said additive stream to said isomerization reaction zone.

13. The process of claim 12 wherein said adsorbent is a clinoptilolite molecular sieve.

14. The process of claim 12 wherein said purified hydrogen stream is passed to said isomerization reaction zone.

* * * * *